United States Patent

Betzing et al.

[11] Patent Number: 4,464,379
[45] Date of Patent: Aug. 7, 1984

[54] INDOL ACETIC ACID DERIVATIVES AND ANTI-INFLAMATORY AND RELATED USES THEREOF

[75] Inventors: Hans Betzing, Kerpen-Horrem; Sigurd Leyck, Brauweiler, both of Fed. Rep. of Germany

[73] Assignee: A. Nattermann & Cie GmbH, Cologne, Fed. Rep. of Germany

[21] Appl. No.: 269,515

[22] Filed: Jun. 1, 1981

[51] Int. Cl.$^3$ .................. C07D 401/12; A61K 31/44
[52] U.S. Cl. .................................... 424/263; 546/273
[58] Field of Search .................... 546/273; 424/263

[56] References Cited

U.S. PATENT DOCUMENTS 4,165,428 8/1979 Noda et al. .................... 546/273

OTHER PUBLICATIONS

Goodman & Gilman, The Pharmacological Basis of Therapeutics, 6th ed., MacMillan, New York, 1980.

Primary Examiner—Henry R. Jiles
Assistant Examiner—Robert C. Whittenbaugh

Attorney, Agent, or Firm—Pearne, Gordon, Sessions, McCoy, Granger & Tilberry

[57] ABSTRACT

The present invention is related to new indol acetic acid derivatives having the general formula

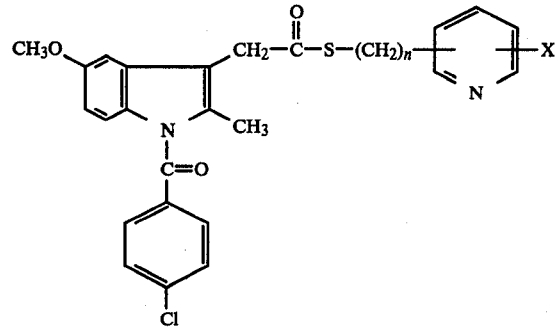

the salts thereof, processes for producing the same and pharmaceutical preparations comprising the same as well as their use as drugs having antithrombotic, antiarteriosclerotic and antiphlogistic activity.

12 Claims, No Drawings

INDOL ACETIC ACID DERIVATIVES AND ANTI-INFLAMATORY AND RELATED USES THEREOF

The present invention is related to new indol acetic acid derivatives having the general formula I

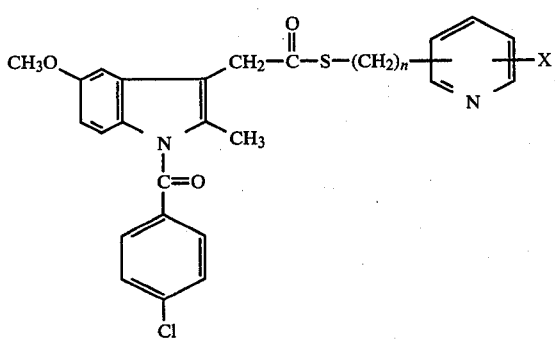

wherein
X is H, F, Cl or a $C_{1-3}$-alkyl group, preferably H, Cl or $CH_3$,
n is an integer from 0 to 3,
and the pharmaceutically compatible, i.e. pharmacologically acceptable salts thereof such as the hydrochloride, fumarate, tartrate, succinate, 2-ketoglutarate, citrate, salicylate or acetylsalicylate.

Most preferred in view of their valuable properties are those compounds of formula I wherein X is hydrogen and n is 1 and the pharmacologically acceptable salts thereof.

The invention is further related to a process for producing the compounds of formula I comprising either
(a) to subject 1-(p-chlorobenzoyl)-5-methoxy-2-methyl-indol-3-acetic acid chloride to reaction with an alkali salt of a compound of the general formula II

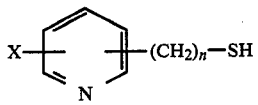

wherein X and n have the same meaning as in formula I, in particular the sodium or potassium salt thereof, in an organic inert solvent such as a cyclic or aliphatic hydrocarbon or halogenated hydrocarbon, in particular toluene, benzene, hexane, chloroform, dimethylformamide or dichloromethane, or
(b) to subject 1-(p-chlorobenzoyl)-5-methoxy-2-methyl-indol-3-acetic acid to reaction with a compound of the above general formula II in the presence of a carbodiimide, in particular N,N'-dicyclohexyl carbodiimide, or in the presence of N,N-dimethyl-phosphoramide dichloride and a weak base (such as pyridine, triethylamine or potassium carbonate) in an organic inert solvent such as toluene, benzene, hexane, dimethylformamide or dichloromethane, or
(c) to subject an 1-(p-chlorobenzoyl)-5-methoxy-2-methyl-indol-3-acetic acid $C_{1-4}$-alkylester, in particular the methyl or ethyl ester, to reaction with a compound of the above general formula II in an organic inert solvent such as toluene, benzene, hexane or dimethylformamide, in particular dichloromethane, in the presence of trimethyl aluminium dissolved in a hydrocarbon,
and converting the resulting product, if desired, to pharmacologically acceptable salts.

The above embodiments of the process according to the present invention are carried out at a temperature ranging from 0° C. to 60° C., preferably from 20° C. to 25° C. The process embodiment (c) preferably is carried out in the presence of a protective gas.

The compounds according to the present invention have an antithrombotic, antiarteriosclerotic, analgetic and in particular antiphlogistic activity. They are in particular useful in the treatment of rheumatic diseases such as arthrosis or chronic polyarthritis. The new compounds are in particular characterized by a very good compatibility since they show a low toxicity and, contrary to known antiphlogistic drugs, no incompatibility to the stomach, i.e. they for instance do not produce ulcera of the stomach or gastrointestinal irritations.

The compounds according to the present invention can be converted into pharmaceutical preparations containing the same in manners known per se. Thus, the active compounds according to the present invention may be used as such or in combination with suitable pharmaceutical diluents and/or carrier materials and may be formulated in usual manners. The compounds according to the present invention may be used both in human or verterinary medicine in any desired form such as in systemic form provided that the formulation and maintenance of a sufficient blood and tissue level is produced. This is possible by oral, rectal or parenteral administration of suitable dosages. It is preferred to use pharmaceutical preparations allowing the administration of single dosages in suitable forms of administration such as tablets, dragées, capsules, suppositories, granulates, solutions, emulsions, suspensions, sols or gels. The dosage of administration in general is between 20 and 50 mg. per day, preferably between 30 and 200 mg. per day and may be administered in a single dose or several doses, preferably in two to three daily doses. Suitable carrier materials for the preparation of orally administratable preparations, for instance tablets, capsules, granulates or powders, are for instance calcium carbonate, calcium phosphate, starch, suggar, lactose, talcum, magnesium stearate, gelatine, polyvinylpyrrolidone, gum-arabic sorbitol, microcrystalline cellulose, polyethylene glycol, carboxymethylcellulose, shellac and the like. Tablets may be coated in usual manners. Liquid products for oral administrations may be aqueous or oily suspensions or solutions. They may also be powderous products with a filler material obtained by deep freeze drying which products are dissolved before administration.

The pharmaceutical preparations according to the present invention may also be suppositories for rectal administration containing pharmaceutically acceptable carrier materials such as polyethyleneglycol, lanolin, coconut butter, witepsol or the like. The products may also be prepared for external administration in the form of ointments or creams which are produced in usual manners with usual additives.

The following examples serve to further illustrate the present invention without however limiting the same thereto.

EXAMPLE 1

Production of
1-(p-chlorobenzoyl)-5-methoxy-2-methyl-3-indol acetic acid-2-pyridylmethylthioester according to process embodiment (b)

6.5 g. (0.018 mol.) of 1-(p-chlorobenzoyl)-5-methoxy-2-methyl-3-indol acetic acid are dissolves in 60 ml. of chloroform. After the addition of 2.9 g. (0.023 mol.) of 2-mercaptomethylpyridine and 4.9 g. (0.023 mol.) of N,N'-dicyclohexyl carbodiimide, the reaction mixture is stirred for 24 hours with the exclusion of moisture. The precipitated material is filtered off and the solvent of the resulting solution is distilled in a vacuum. The resulting residue is subjected to chromatography over a silicic acid gel column using a 1:1-mixture of chloroform and hexane as eluant.

Yield: 7.1 g. (84.7% of the theoretical) F.p.: 153° to 154° C.

Elementary analysis: $C_{25}H_{22}O_3N_2SCl$ Calculated: C 63.21%, H 4.57%, N 5.88%, S 6.72%. Found: C 64.44%, H4.74%, N 6.01%, S 6.88%.

EXAMPLE 2

Preparation of
1-(p-chlorobenzoyl)-5-methoxy-2-methyl-3-indol acetic acid-3-pyridylmethylthioester according to process embodiment (a)

34.2 g. (0.1 mol.) of 1-(p-chlorobenzoyl)-5-methoxy-2-methyl-3-indol acetic acid chloride (produced from the corresponding indol acetic acid derivative by reaction with oxalylchloride) are dissolved in 500 ml. of anhydrous dichloromethane. 16.2 g. (0.12 mol.) of the sodium salt of 3-mercaptomethylpyridine are added thereto with the exclusion of moisture and the reaction mixture is stirred for 6 hours at room temperature with the exclusion of moisture. The precipitated sodium chloride is filtered off and the solvent of the resulting solution is distilled off in a vacuum. The resulting reaction product is purified by means of chromatography on silicic acid gel as adsorbing agent and chloroform as eluant.

Yield: 33 g. (70.8% of the theoretical) F.p.: 127° to 128° C. Hydrochloride: F.p. 159° to 161° C. (from methanol/ether).

EXAMPLE 3

Production of
1-(p-chlorobenzoyl)-5-methoxy-2-methyl-3-indol acetic acid-3-(3-pyridyl)-propylthioester by process embodiment (c)

5.76 g. (0.02 mol.) of trimethylaluminum (corresponding to 8 ml. of a 25% solution of trimethylaluminum in hexane) are dissolved in 40 ml. of anhydrous methylenechloride and cooled to 0° C. 2.74 g. (0.02 mol.) of 3-(3-pyridyl)-1-propylmercaptane are added thereto with stirring, exclusion of moisture and in a nitrogen gas atmosphere. The reaction mixture is heated to room temperature within 15 to 20 minutes whereafter a solution of 8.12 g. (0.02 mol.) of 1-(p-chlorobenzoyl)-5-methoxy-2-methyl-1-indol acetic acid ethylester dissolved in 5 ml. of methylene chloride is added thereto. The reaction mixture is stirred, at the same time introducing nitrogen gas into the reaction vessel as protective gas, stirring being continued until the reaction is finished as controlled by thin layer chromatography. About 100 ml. of ether are added and the resulting solution is first shaken with a 3% aqueous hydrochloric acid and then with a 5% aqueous lye.

The ethereal phase is dried over anhydrous sodium sulfate and the solvent is distilled off. The remaining residue is purified by chromatography using a column containing silicic acid gel as adsorption agent and chloroform as eluant.

Yield: 8.5 g. (89.9% of the theoretical) of a slightly yellow hygroscopic product having the RF-value 0.813 (using prefabricated silicic acid gel plates), eluant: chloroform/methanol 95:5

Molecular analysis: $C_{27}H_{26}O_3N_2S_1Cl_1$ Calculated: C 65.65%, H 5.31%, N 5.6%, S 6.48% Found: C 63.91%, H 5.18%, N 5.42%, S 6.52%

The salicylate melts at F.p.: 224° to 225° C.

In accordance with examples 1 to 3 the following compounds have been prepared:

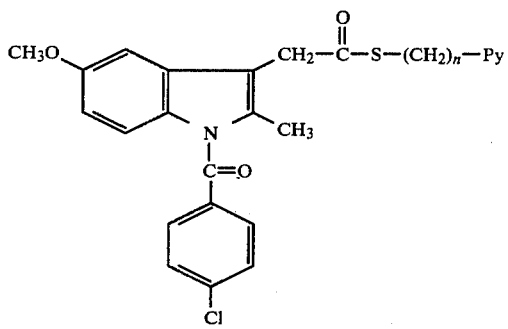

| Example | n | Py | Salt | F.p. (°C.) |
|---|---|---|---|---|
| 4 | 2 | 2-pyridyl | hydrochloride | 125–126+ |
| 5 | 1 | 4-pyridyl | — | 207–209 |
| 6 | 1 | 6-methyl-3-pyridyl | — | 136–138 |
| 7 | 0 | 2-pyridyl | — | 175–176 |
| 8 | 1 | 6-chloro-2-pyridyl | — | 168–170 |
| 9 | 1 | 5-fluoro-2-pyridyl | — | 165–166 |
| 10 | 1 | 3-pyridyl | fumarate | 127 |
| 11 | 2 | 2-pyridyl | acetylsalicilate | 210–211 |

+hydroscopic

EXAMPLE 12

| Tablets | |
|---|---|
| 1-(p-Chlorobenzoyl)-5-methoxy-2-methyl-3-indol acetic acid-3-pyridylmethylthioester | 30 mg. |
| lactose | 150 mg. |
| crystalline cellulose | 50 mg. |
| calcium carboxymethylcellulose | 7 mg. |
| magnesium stearate | 3 mg. |

The above components are mixed in usual manners, granulated and filled into hard gelatine capsules.

EXAMPLE 13

| Capsules | |
|---|---|
| 1-(p-Chlorobenzoyl)-5-methoxy-2-methyl-3-indol acetic acid-3-pyridylmethylthioester | 50 mg. |
| talcum | 5 mg. |
| Aerosil 200 | 10 mg. |

The above components are mixed, granulated and filled into hard gelatine capsules.

What we claim is:

1. Indol acetic acid derivative having the general formula I

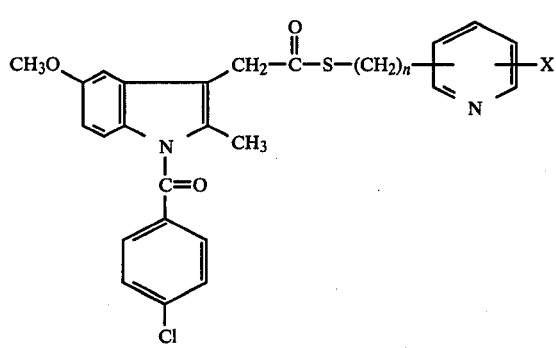

wherein

X is H, F, Cl or a $C_{1-3}$-alkyl group n is an integer from 0 to 3, and the pharmacologically acceptable salts thereof.

2. 1-(p-Chlorobenzoyl)-5-methoxy-2-methyl-3-indol acetic acid-2-pyridylmethylthioester and the pharmacologically acceptable salts thereof.

3. 1-(p-Chlorobenzoyl)-5-methoxy-2-methyl-3-indol acetic acid-3-pyridylmethylthioester and the pharmacologically acceptable salts thereof.

4. 1-(p-Chlorobenzoyl)-5-methoxy-2-methyl-3-indol acetic acid-2-(3-pyridyl)-ethylthioester and the pharmacologically acceptable salts thereof.

5. 1-(p-Chlorobenzoyl)-5-methoxy-2-methyl-3-indol acetic acid-3-(3-pyridyl)-propylthioester and the pharmacologically acceptable salts thereof.

6. 1-(p-Chlorobenzoyl)-5-methoxy-2-methyl-3-indol acetic acid-4-pyridylmethylthioester and the pharmacologically acceptable salts thereof.

7. 1-(p-Chlorobenzoyl)-5-methoxy-2-methyl-3-indol acetic acid-(6-methyl-3-pyridyl)-methylthioester and the pharmacologically acceptable salts thereof.

8. 1-(p-Chlorobenzoyl)-5-methoxy-2-methyl-3-indol acetic acid-2-pyridylthioester and the pharmacologically acceptable salts thereof.

9. 1-(p-Chlorobenzoyl)-5-methoxy-2-methyl-3-indol acetic-(6-chloro-2-pyridyl)-methylthioester and the pharmacologically acceptable salts thereof.

10. Process for the treatment of humans suffering from rheumatic diseases comprising administering to such humans a compound according to claim 1, 2, 3, 4, 5, 6, 7, 8 or 9 in an amount of from 20 to 500 mg. per day in a single dose or in several doses.

11. Process according to claim 10 wherein the compound is administered in two to three doses per day.

12. Process according to claim 10 wherein the compound is administered in a daily dose amounting to from 30 to 200 mg.

* * * * *